(12) United States Patent
Chen et al.

(10) Patent No.: US 10,223,606 B2
(45) Date of Patent: Mar. 5, 2019

(54) 3-D INTRAORAL MEASUREMENTS USING OPTICAL MULTILINE METHOD

(71) Applicant: Carestream Dental Technology Topco Limited, London (GB)

(72) Inventors: Qinran Chen, Shanghai (CN); Yanbin Lu, Shanghai (CN); James R. Milch, Penfield, NY (US); Victor C. Wong, Rochester, NY (US)

(73) Assignee: Carestream Dental Technology Topco Limited, London (GB)

( * ) Notice: Subject to any disclaimer, the term of this patent is extended or adjusted under 35 U.S.C. 154(b) by 0 days.

(21) Appl. No.: 15/504,889

(22) PCT Filed: Aug. 28, 2014

(86) PCT No.: PCT/US2014/053039
§ 371 (c)(1),
(2) Date: Feb. 17, 2017

(87) PCT Pub. No.: WO2016/032470
PCT Pub. Date: Mar. 3, 2016

(65) Prior Publication Data
US 2017/0277965 A1    Sep. 28, 2017

(51) Int. Cl.
*H04N 13/00* (2018.01)
*A62B 1/04* (2006.01)
(Continued)

(52) U.S. Cl.
CPC ............ *G06K 9/2027* (2013.01); *G06T 7/521* (2017.01); *G06T 7/60* (2013.01); *G06T 2207/10152* (2013.01); *G06T 2207/30036* (2013.01)

(58) Field of Classification Search
None
See application file for complete search history.

(56) References Cited

U.S. PATENT DOCUMENTS

| 5,372,502 A | 12/1994 | Massen et al. |
| 5,650,621 A | 7/1997 | Tsuneta et al. |

(Continued)

FOREIGN PATENT DOCUMENTS

| CN | 101466998 A | 6/2009 |
| CN | 101862182 A | 10/2010 |

(Continued)

OTHER PUBLICATIONS

International Search Report, dated Feb. 1, 2013 for International Application No. PCT/US2012/052178, 2 pages.
(Continued)

*Primary Examiner* — Heather R Jones

(57) ABSTRACT

A method for mapping a sensor pixel array to an illumination pixel array according to a surface forms a group mapping by assigning each pixel in a on the sensor array to a group that has a group width defined by p adjacent pixels on the illumination pixel array by projecting and recording a first and a second multiple group index image with a first and second pattern of lines. Lines appearing in both first and second pattern are spaced by a first distance that is a first multiple of group width p, and lines that appear only in either pattern are evenly spaced by a second distance that exceeds the first distance. A subset of p multiline images are projected, each projecting a line within each group. Lines in one of the multiline images are correlated with lines from the group index images to generate the group mapping.

15 Claims, 13 Drawing Sheets

(51) Int. Cl.
*G06K 9/20* (2006.01)
*G06T 7/521* (2017.01)
*G06T 7/60* (2017.01)

(56) References Cited

U.S. PATENT DOCUMENTS

| | | | |
|---|---|---|---|
| 6,510,244 B2 | 1/2003 | Proesmans et al. | |
| 6,754,370 B1 | 6/2004 | Hall-Holt et al. | |
| 7,126,699 B1 | 10/2006 | Wihl et al. | |
| 7,146,036 B2 | 12/2006 | An Chang et al. | |
| 9,295,532 B2 | 3/2016 | Milch | |
| 9,675,428 B2 * | 6/2017 | Wu | A61C 9/006 |
| 9,922,459 B2 * | 3/2018 | Graham | G06T 15/00 |
| 2005/0046873 A1 | 3/2005 | Suzuki | |
| 2005/0099638 A1 | 5/2005 | Quadling et al. | |
| 2005/0254726 A1 | 11/2005 | Fuchs et al. | |
| 2006/0083422 A1 | 4/2006 | Ernst et al. | |
| 2006/0210145 A1 | 9/2006 | Lee et al. | |
| 2007/0057946 A1 | 3/2007 | Albeck et al. | |
| 2007/0091319 A1 | 4/2007 | Sonda et al. | |
| 2009/0103103 A1 | 4/2009 | Berner | |
| 2009/0238449 A1 * | 9/2009 | Zhang | G01B 11/2536 382/165 |
| 2009/0322859 A1 | 12/2009 | Shelton et al. | |
| 2010/0034429 A1 | 2/2010 | Drouin et al. | |
| 2010/0085636 A1 | 4/2010 | Berner | |
| 2010/0253773 A1 | 10/2010 | Oota et al. | |
| 2010/0268069 A1 | 10/2010 | Liang | |
| 2010/0311005 A1 | 12/2010 | Liang | |
| 2011/0050859 A1 | 3/2011 | Kimmel et al. | |
| 2011/0080471 A1 | 4/2011 | Song et al. | |
| 2013/0120533 A1 | 5/2013 | Milch | |

FOREIGN PATENT DOCUMENTS

| | | |
|---|---|---|
| CN | 101883520 A | 11/2010 |
| CN | 103917160 B | 8/2016 |
| CN | 106796727 A | 5/2017 |
| EP | 2 051 042 B1 | 11/2010 |
| EP | 2 775 914 B1 | 2/2018 |
| EP | 3 195 253 B1 | 6/2018 |
| JP | 03-293507 A | 12/1991 |
| JP | 2004-226160 A | 8/2004 |
| JP | 2005-003409 A | 1/2005 |
| JP | 2009-098146 A | 5/2009 |
| JP | 2010-243508 A | 10/2010 |
| JP | 2011-504586 A | 2/2011 |
| JP | 2011-047931 A | 3/2011 |
| JP | 2012-042332 A | 3/2012 |
| JP | 2014-534448 A | 12/2014 |
| JP | 6072814 B2 | 2/2017 |
| JP | 2017-532989 A | 11/2017 |
| KR | 10-2014-0090620 A | 7/2014 |
| KR | 10-2017-0045232 A | 4/2017 |
| WO | 2009/063087 A2 | 5/2009 |
| WO | 2011/013373 A1 | 2/2011 |
| WO | 2013/070301 A1 | 5/2013 |
| WO | 2016/032470 A1 | 3/2016 |

OTHER PUBLICATIONS

Supplemental European Search Report, Application No. EP1284732, dated Jun. 19, 2015, 2 pages.
Guhring, Jens "Dense 3-D surface acquisition by structured light using off-the-shelf components", Videometrics and Optical Methods for 3D Shape Measurement, Proceedings of SPIE, vol. 4309 (2001) pp. 220-231.
S. Logozzo, G. Franceschini, A. Kilpelä, M. Caponi, L. Governi, L. Blois: A Comparative Analysis of Intraoral 3d Digital Scanners for Restorative Dentistry. *The Internet Journal of Medical Technology*. 2011, vol. 5, No. 1, DOI: 10.5580/1b90, 19 pages, http://www.ispub.com:80/journal/the-internet-journal-of-medical-technology/volume-5-number-1/a-comparative-analysis-of-intraoral-3d-digital-scanners-for-restorative-dentistry.html.
S. Barone, et al., "3D Maxillofacial Model Creation for Computer-guided Treatments in Oral Rehabilitation", Virtual Systems and Multimedia (VSMM), 18th International Conference on IEEE, 2012, pp. 421-428.
Communication pursuant to Rules 161(1) and 162 EPC for EP Application Serial No. 14772488.4 dated Apr. 4, 2017, 2 pages.
Communication under Rule 71(3) EPC for EP Application Serial No. 14772488.4 dated Jan. 26, 2018, 45 pages.
Notification of Reasons for Refusal received for Japanese Application Serial No. 2017-511174 dated Jun. 12, 2018, 7 pages (including English Translation).
International Search Report and Written Opinion received for PCT Application Serial No. PCT/US2014/053039 dated May 28, 2015, 10 pages.
International Preliminary Report on Patentability received for PCT Application Serial No. PCT/US2014/053039 dated Mar. 9, 2017, 8 pages.
International Preliminary Report on Patentability received for PCT Application Serial No. PCT/US2012/052178 dated May 22, 2014, 6 pages.
Communication under Rule 71(3) EPC for EP Application Serial No. 12847432.7 dated Sep. 22, 2017, 106 pages.
Non-Final Office Action received for U.S. Appl. No. 13/293,308 dated Sep. 25, 2014, 36 pages.
Final Office Action received for U.S. Appl. No. 13/293,308 dated Jun. 12, 2015, 12 pages.
Notice of Allowance received for U.S. Appl. No. 13/293,308 dated Jan. 28, 2016, 32 pages.
Non-Final Office Action received for U.S. Appl. No. 13/525,590 dated Jan. 2, 2015, 49 pages.
Final Office Action received for U.S. Appl. No. 13/525,590 dated Jun. 29, 2015, 13 pages.
Non-Final Office Action received for U.S. Appl. No. 13/525,590 dated Dec. 1, 2015, 13 pages.
Notice of Allowance received for U.S. Appl. No. 13/525,590 dated Mar. 31, 2016, 42 pages.
First Office Action received for Chinese Application Serial No. 201280055128.7 dated Jun. 2, 2015, 15 pages (including English Translation).
Second Office Action received for Chinese Application Serial No. 201280055128.7 dated Mar. 10, 2016, 9 pages (including English Translation).
Notification to Grant Patent Right for Invention received for Chinese Application Serial No. 201280055128.7 dated Jun. 21, 2016, 3 pages (including English Translation).
Notification of Reasons for Refusal received for Japanese Application Serial No. 2014-541042 dated Apr. 19, 2016, 7 pages (including English Translation).
Decision to Grant a Patent received for Japanese Application Serial No. 2014-541042 dated Dec. 13, 2016, 3 pages (including English Translation).

* cited by examiner

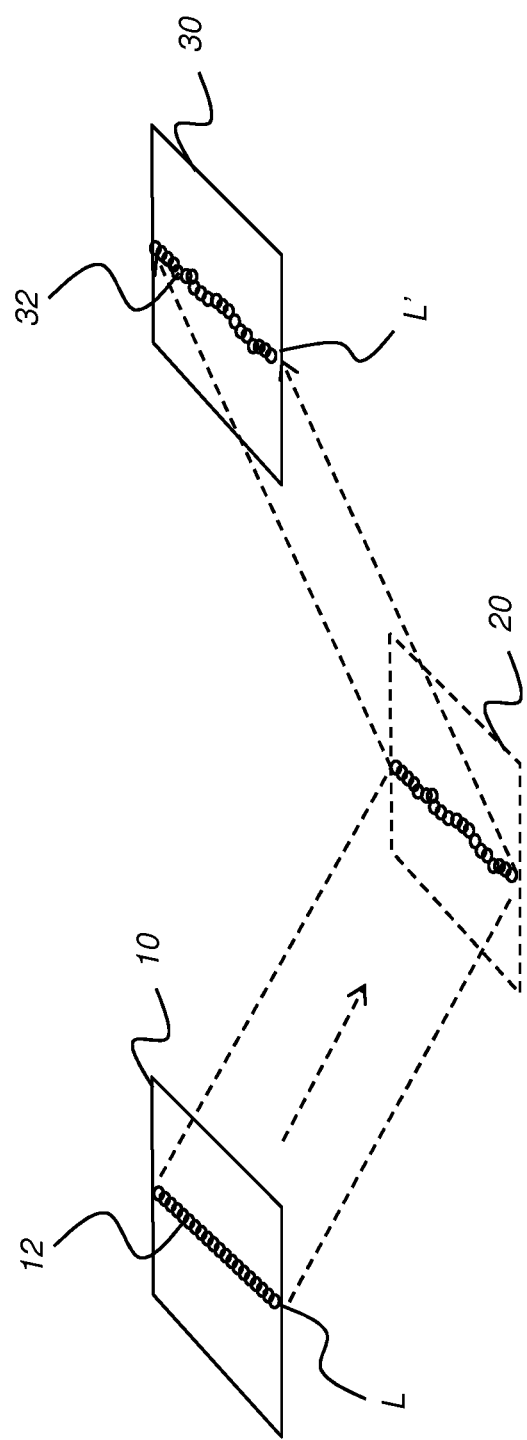

3-D INTRAORAL MEASUREMENTS USING OPTICAL MULTILINE METHOD

CROSS REFERENCE TO RELATED APPLICATIONS

This application claims the benefit of and is a US national phase filing of PCT application No. PCT/US2014/0053039 filed Aug. 28, 2014 that is entitled, "3-D INTRAORAL MEASUREMENTS USING OPTICAL MULTILINE METHOD", in the name of Qinran Chen et al.; the disclosure of this priority application is incorporated herein by reference in its entirety.

TECHNICAL FIELD

The invention relates generally to the field of surface shape imaging and more particularly relates to intraoral surface imaging and measurement using patterned illumination.

BACKGROUND

A number of techniques have been developed for obtaining surface contour information from various types of objects in medical, industrial, and other applications. Optical 3-dimensional (3-D) measurement methods provide shape and depth information using images obtained from patterns of light directed onto a surface. Various types of imaging methods generate a series of light patterns and use focus or triangulation to detect changes in surface shape over the illuminated area.

Fringe projection imaging uses patterned or structured light and triangulation to obtain surface contour information for structures of various types. In fringe projection imaging, a pattern of lines of an interference fringe or grating is projected toward the surface of an object from a given angle. The projected pattern from the surface is then viewed from another angle as a contour image, taking advantage of triangulation in order to analyze surface information based on the appearance of contour lines. Phase shifting, in which the projected pattern is incrementally spatially shifted for obtaining additional measurements at the new locations, is typically applied as part of fringe projection imaging, used in order to complete the contour mapping of the surface and to increase overall resolution in the contour image.

Fringe projection imaging has been used effectively for surface contour imaging of solid, highly opaque objects and has been used for imaging the surface contours for some portions of the human body and for obtaining detailed data about skin structure. However, a number of technical obstacles have prevented effective use of fringe projection imaging of the tooth. One particular challenge with dental surface imaging relates to tooth translucency. Translucent or semi-translucent materials in general are known to be particularly troublesome for fringe projection imaging. Subsurface scattering in translucent structures can reduce the overall signal-to-noise (S/N) ratio and shift the light intensity, causing inaccurate height data. Another problem relates to high levels of reflection for various tooth surfaces. Highly reflective materials, particularly hollowed reflective structures, can effectively reduce the dynamic range of this type of imaging.

From an optical perspective, the structure of the tooth itself presents a number of additional challenges for fringe projection imaging. Teeth can be wet or dry at different times and along different surfaces and portions of surfaces. Tooth shape is often irregular, with sharp edges. As noted earlier, teeth interact with light in a complex manner. Light penetrating beneath the surface of the tooth tends to undergo significant scattering within the translucent tooth material. Moreover, reflection from opaque features beneath the tooth surface can also occur, adding noise that degrades the sensed signal and thus further complicates the task of tooth surface analysis.

One corrective measure that has been attempted to make fringe projection workable for contour imaging of the tooth is application of a coating that changes the reflective characteristics of the tooth surface itself. To compensate for problems caused by the relative translucence of the tooth, a number of conventional tooth contour imaging systems apply a paint or reflective powder to the tooth surface prior to surface contour imaging. For the purposes of fringe projection imaging, this added step enhances the opacity of the tooth and eliminates or reduces the scattered light effects noted earlier. However, there are drawbacks to this type of approach. The step of applying a coating powder or liquid adds cost and time to the tooth contour imaging process. Because the thickness of the coating layer is often non-uniform over the entire tooth surface, measurement errors readily result. More importantly, the applied coating, while it facilitates contour imaging, can tend to mask other problems with the tooth and can thus reduce the overall amount of useful information that can be obtained.

Even where a coating or other type of surface conditioning of the tooth is used, however, results can be disappointing due to the pronounced contours of the tooth surface. It can be difficult to provide sufficient amounts of light onto, and sense light reflected back from, all of the tooth surfaces. The different surfaces of the tooth can be oriented at 90 degrees relative to each other, making it difficult to direct enough light for accurately imaging all parts of the tooth.

A number of problems complicate mapping of an illumination array to sensor circuitry for accurate surface contour measurement. Because multiple images must be captured with the teeth in the same position, any type of movement of the camera or of the patient can complicate the measurement task or require re-imaging and additional measurement time. Thus, it is advantageous to reduce the number of images that need to be obtained for accurate mapping. At the same time, however, measurement improves when multiple images can be obtained and their respective data correlated. Given these conflicting considerations, it can be seen that there are advantages to more efficient pixel mapping techniques that obtain a significant amount of data from a small number of images.

SUMMARY

An aspect of this application is to address, in whole or in part, at least the foregoing and other deficiencies in the related art.

Another aspect of this application to provide, in whole or in part, at least the advantages described herein.

It is another aspect of this application is to advance the art of dental imaging.

An object of the present invention is to advance the art of surface contour detection of teeth and related intraoral structures. Embodiments of the present invention provide 3-D surface information about a tooth by illuminating the tooth surface with an arrangement of light patterns that help to more closely map pixel locations on a digital imaging array with pixel locations from an illumination device. Advantageously, the present invention can be used with known illumination and imaging component arrangements and is adapted to help reduce ambiguity of sensed patterns when compared against conventional contour detection methods.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for mapping a sensor pixel array to an illumination pixel array according to a surface, the method executed at least in part on a computer and that can include forming a group mapping by assigning each pixel in a plurality of pixels on the sensor array to a corresponding group of an ordered set of groups, wherein each group has a group width defined by a set of p adjacent pixels on the illumination pixel array and the ordered set has k groups by: projecting and recording a first multiple group index image with a first pattern of lines and a second multiple group index image with a second pattern of lines, wherein there are lines that appear in both the first and second pattern, and wherein lines that appear in both first and second patterns are evenly spaced from each other by a first distance that is a first multiple of group width p wherein the first multiple is an integer greater than 1, and lines that appear only in either the first or the second pattern are evenly spaced from each other by a second distance that is a second multiple of group size and that exceeds the first distance; projecting and recording a subset of a set of p multiline images onto the surface, wherein each multiline image projects a line within each group and wherein the projected lines in each of the subset of p multiline images are evenly spaced apart by a group width of p pixels; and correlating lines in one of the recorded multiline images with lines from the first and second multiple group index images to generate the group mapping for all k groups and storing the correlation in a computer-accessible memory.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 1 is a schematic diagram that shows mapping a sensor pixel array to an illumination array according to a surface.

DETAILED DESCRIPTION OF THE EMBODIMENTS

Figure 2B:
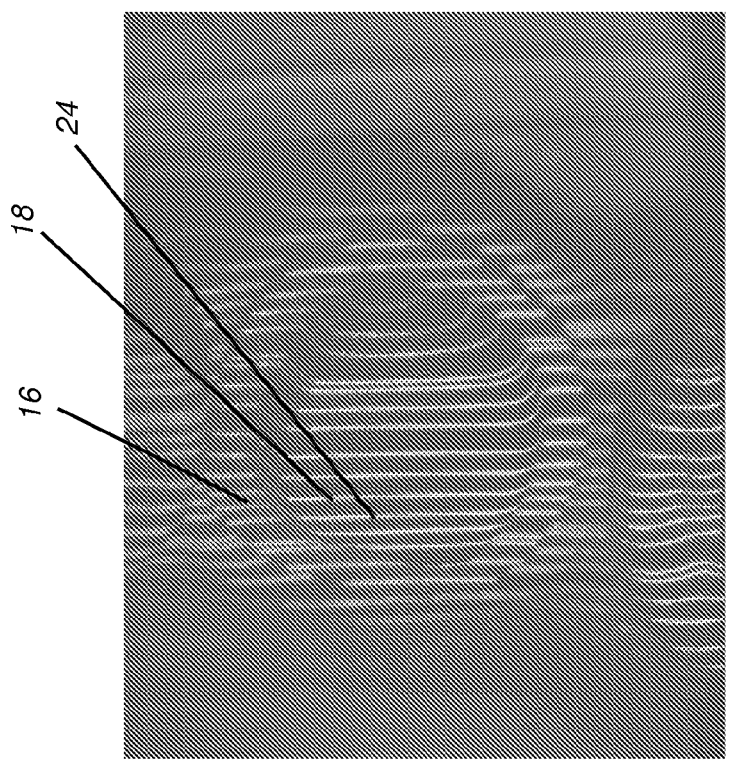
FIG. 2B shows illumination of a tooth surface with multiple lines of light.

The following is a detailed description of exemplary embodiments, reference being made to the drawings in which the same reference numerals identify the same elements of structure in each of the several figures.

Where they are used, the terms "first", "second", and so on, do not necessarily denote any ordinal, sequential, or priority relation, but are simply used to more clearly distinguish one element or set of elements from another.

In the context of the present disclosure, the terms "viewer", "operator", and "user" are considered to be equivalent and refer to the viewing practitioner or technician or other person who views and manipulates an image, such as a dental image, on a display monitor.

The term "set", as used herein, refers to a non-empty set, as the concept of a collection of elements or members of a set is widely understood in elementary mathematics. The term "subset", unless otherwise explicitly stated, is used herein to refer to a non-empty subset, that is, to a subset of the larger set, having one or more members. For a set S, a subset may comprise the complete set S, including all members. A "proper subset" of set S is strictly contained in set S and excludes at least one member of set S. However, unless specifically designated as a proper subset, a subset in the context of the present disclosure has the broader definition of being non-empty and containing at least one, or more, or all members of a set.

The schematic diagram of FIG. 1 shows, with the example of a single line of light L, how patterned light is used for obtaining surface contour information. A mapping is obtained as an illumination array 10 projects or directs a pattern of light onto a surface 20 and a corresponding image of a reflected line L' is formed on an imaging sensor array 30. Each pixel 32 on imaging sensor array 30 maps to a corresponding pixel 12 on illumination array 10 according to modulation by surface 20. Shifts in pixel position, as represented in FIG. 1, yield useful information about the contour of surface 20. It can be appreciated that the basic pattern shown in FIG. 1 can be implemented in a number of ways, using a variety of illumination sources and sequences for projecting the images and using one or more different types of sensor arrays 30 for obtaining or acquiring image data. Illumination array 10 can utilize any of a number of types of arrays used for light modulation, such as a liquid crystal array or digital micromirror array, such as that provided using the Digital Light Processor or DLP device from Texas Instruments, Dallas, Tex. This type of spatial light modulator is used in the illumination path to change the projected light pattern as needed for the mapping sequence.

Figure 2A:
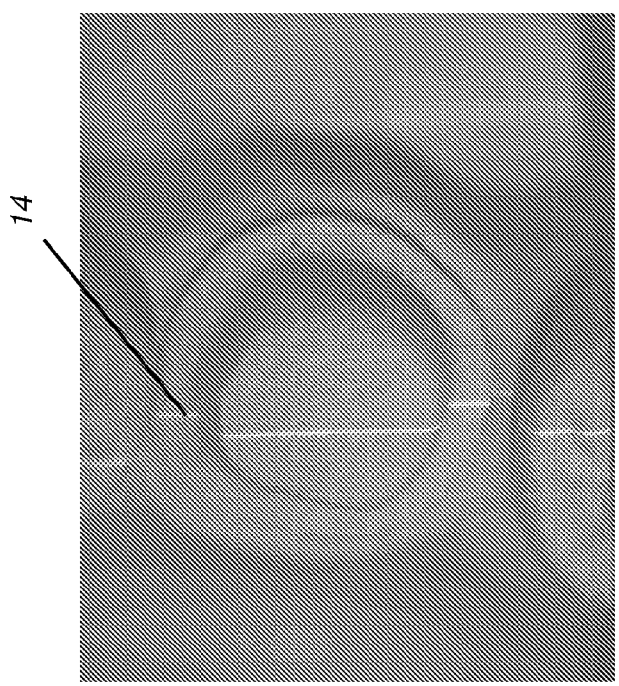
FIG. 2A shows illumination of a tooth surface with a single line of light.

FIGS. 2A and 2B show aspects of one problem with conventional approaches for using patterned light to obtain surface structure information from the human tooth. FIG. 2A shows illumination with a single line of light 14 onto the tooth, with pronounced shifting of the illumination at the tooth edges. Projection of a single line in this manner, scanned across the tooth and imaged at numerous points during the scan, can provide accurate information about portions of the surface area; however, some information is lost even with this method, such as where line segments are separated from each other. FIG. 2B shows surface imaging using a pattern with multiple lines of light. Where there are abrupt transitions along the surface, it can be difficult to positively identify the segments that correspond to each projected line and mismatches can easily occur, leading to inaccurate conclusions about surface characteristics. For example, it can be difficult to determine whether line segment 16 is from the same line of illumination as line segment 18 or adjacent line segment 24.

Embodiments of the present invention address the problem of surface contour mapping using a sequence of projected images that help to better correlate pixels on the imaging sensor array with projected lines from the illumination array. To do this, embodiments of the present invention use an arrangement of binary images in order to group pixels on the imaging sensor array with corresponding pixels on the illumination pixel array. A group mapping is formed by assigning pixels on the sensor array to an ordered set of groups, each group having a fixed number of pixels (e.g., the same number of pixels). The group mapping can be stored as a particular data structure or may be otherwise represented in data that relates each pixel to a particular group structure, using mapping techniques well known to those skilled in the data representation arts. In the context of the present disclosure, the terms "group map" and "group mapping" are considered to be equivalent, since the relationship of pixels and groups can be represented and stored in any of a number of ways.

Figure 3:
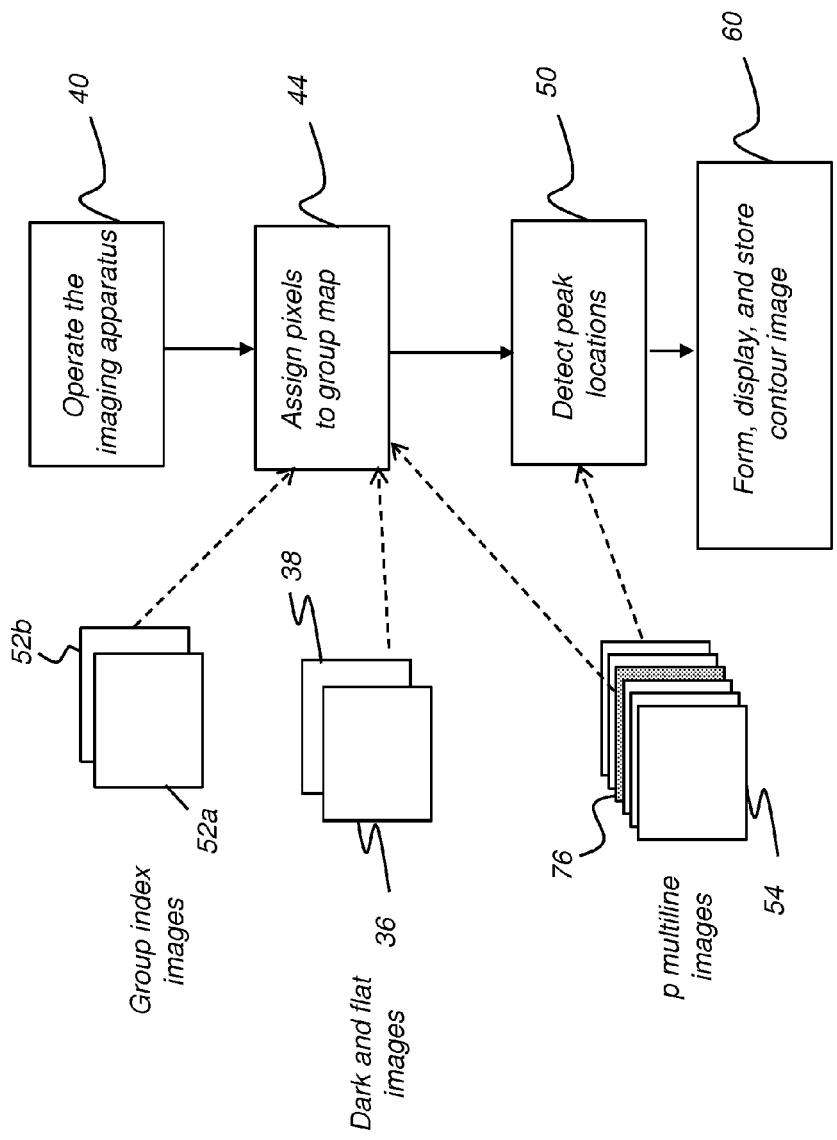
FIG. 3 is a logic flow diagram that shows a sequence for obtaining surface contour image data according to an embodiment of the present invention.

Referring to the flow diagram of FIG. 3, there is shown a sequence of image projection, detection, and processing steps used for surface contour detection and executed at least in part on a computer according to an embodiment of the present disclosure. In an image capture step 40, the operator positions the imaging apparatus and captures a series of patterned illumination images. The images can include or consist of two group index images 52a and 52b, optional dark and flat (bright) images 36 and 38, respectively, and a number p of multiline images 54 and can be captured in any order. In an alternate embodiment, more than two group index images can be used. In an alternate embodiment, a subset of the p multiline images 54 and can be captured or used. Once the images are captured, a pixel assignment step 44 executes, in which pixels on the image sensor array are assigned to a group map or mapping that corresponds to pixels on the illumination array. Additional, optional dark image 36, with no illumination, and flat image 38 with full frame illumination can also be obtained to help in signal processing, as described subsequently.

Continuing with the sequence of FIG. 3 for forming the contour image, a set of p multiline images 54 is also obtained, from which peak locations, that is, locations of highest intensity indicative of surface contour, can be detected in a location detection step 50. Alternately, a proper subset of the set of p multiline images can be obtained for use in the location detection step 50, with correspondingly lower resolution in the peak location detection results; in this case, interpolation can be applied to fill in the data for the line peaks within each group that are not projected. A mapping step 60 then forms, displays, and stores the contour image in a memory, such as in a temporary display memory that is associated with a display monitor, for example. Optionally, one or more of the group index images or multiline images can also be displayed.

Relative to FIG. 1, each group index image 52a, 52b has an arrangement of lines that are one pixel wide on illumination array 10. A multiline image also has one or more bright bands that are one pixel wide on illumination array 10. The multiline image has at least one bright-to-dark or dark-to-bright transition within each group of pixels.

Figure 4:
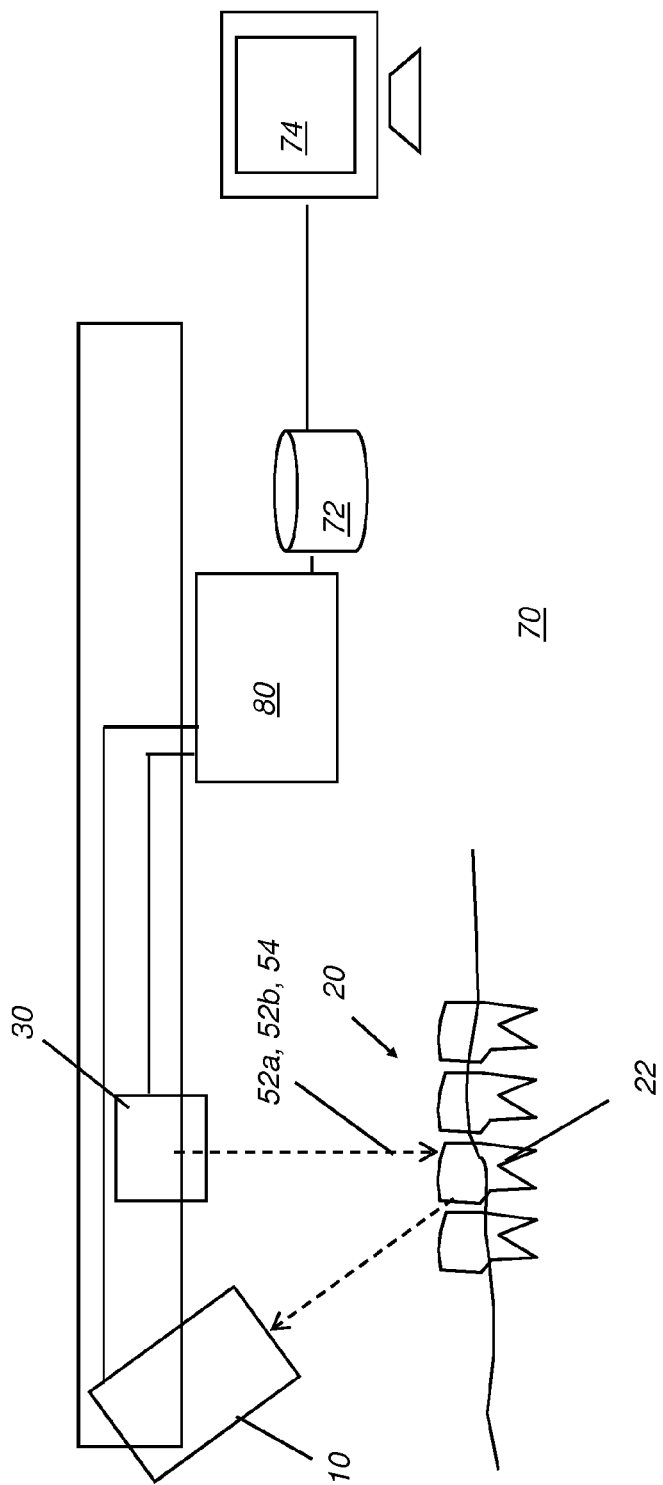
FIG. 4 is a schematic diagram showing an imaging apparatus.

The schematic diagram of FIG. 4 shows an imaging apparatus 70 for projecting and capturing at least the group index images 52a and 52b and one or more multiline images 54. A control logic processor 80, or other type of computer can control the operation of illumination array 10 and imaging sensor array 30. Image data from surface 20, such as from a tooth 22, is obtained from imaging sensor array 30 and stored in a memory 72. Control logic processor 80 processes the received image data and stores the mapping in memory 72. The resulting image from memory 72 is then optionally displayed on a display 74. Memory 72 may also include a display buffer.

For the explanation of group and pixel mapping that follows:
(1) the numerical labeling of illuminator lines is assumed to increase from right to left on the imaging sensor array; a monotonic rule states that the group number must increase from right to left along a row; and
(2) there are assumed to be multiple (at least 2 or 3) imaging sensor array pixels for every illuminator array pixel, although a single pixel could be used.

It should be emphasized that the order of numerical labeling can alternately be increasing from left to right, with corresponding changes to the description.

Forming the Group Mapping

Figure 5:
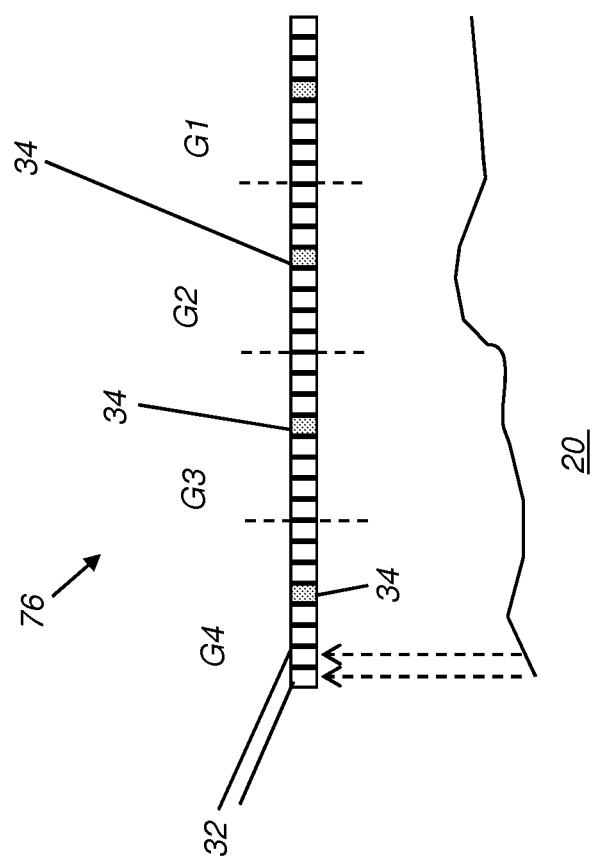
FIG. 5 is a schematic diagram that shows part of a row of pixels on the imaging sensor array.

Schematic diagrams of FIGS. 5-8 show various aspects of the process for forming the group map according to an embodiment of the present invention. FIG. 5 shows part of a row of pixels 32 on imaging sensor array 30 corresponding to positions on surface 20. Each group has a predetermined number p of adjacent pixels 32, with eight pixels 32 per group in the example mapping that is shown. The number p can also be some other number of pixels that make up a group, such as 10 or 12 pixels. Vertical dashed lines in FIG. 5 indicate group boundaries. At a group boundary, wherein each group hasp pixels numbered from 0, 1, 2, ... (p−1), the (p−1)th pixel of one group is adjacent to the 0th pixel of the next, or adjacent, group in the row; the space between these two adjacent pixels, with one pixel in each of two adjacent groups, defines a group boundary. The group boundary is considered to be "shared" by two adjacent groups. Each group also has a center pixel 34, shown shaded in FIG. 5. The center pixel 34 is the pixel with number (p/2). Thus, where the group has 8 pixels (p=8) as in the example of FIG. 5, the center pixel is the pixel numbered 4. For reference with respect to the present disclosure, the arrangement shown in FIG. 5, with the p/2 pixel illuminated within each group, is termed a centered multiline image 76. Thus, in one embodiment, the centered multiline image 76 is the only one of the multiline images that is used for both pixel mapping and group mapping, as represented in FIG. 3 and as described in more detail subsequently.

Geometrically, when moving from one side of the image to the other along a row of pixels for certain exemplary embodiments, the group number must change monotonically. (The numbers on different rows may not align, but within each row, they are monotonic.) This makes it possible to 'proofread' the group numbers on each row, discarding places where noise has disturbed the expected monotonic increase of group number.

The group map is generated using images that illuminate and project selected pixels (e.g., center pixels) from one or more groups. When center pixels are used for one or more groups, these images can be referred to as "centerline" images. In one embodiment, referring back to the logic flow diagram of FIG. 3, this can includes each of the group index images 52a and 52b and a corresponding one of the p multiline images, specifically, centered multiline image 76.

Group Index Images

Figure 6:
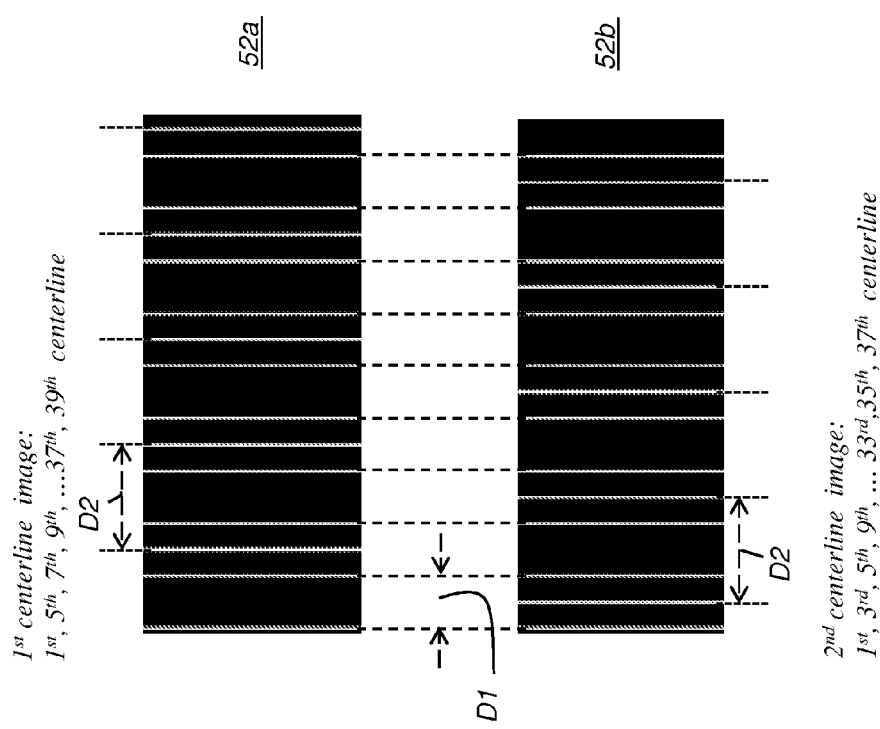
FIG. 6 shows two group index images for group mapping according to an embodiment of the present disclosure.

Each of the group index images 52a and 52b is preferably a centerline image that projects a pattern of lines corresponding to some of the center pixels in the illumination array. An exemplary arrangement using two group index images 52a and 52b is shown in FIG. 6. Images 52a and 52b are left-aligned. For this example, there are a total of 40 groups, numbered from 0 through 39. Here, centerlines are only projected for odd-numbered groups (1, 3, 5, 7, . . . ); centerlines for even numbered groups (0, 2, 4, 6, 8, . . . ) are not projected in group index images 52a and 52b but are provided by one of the multiline images, as described subsequently.

In the example of FIG. 6, group index image 52a projects centerlines for odd-numbered groups 1, 5, 7, 9, . . . 37, 39. Group index image 52b projects centerlines for odd-numbered groups 1, 3, 5, 9, . . . 35, 37. Dashed lines extend between centerlines for the same groups in both group index images 52a and 52b. Thus, for example, both images have centerlines in identical positions, for groups 1, 5, 9, . . . 37. A distance D1 between these commonly projected centerlines is 4 groups wide. It can be seen that the common centerlines are equidistant from each other by a first distance D1 that is a first multiple of group size.

In the FIG. 6 arrangement, dotted lines indicate groups that have centerlines only in group index image 52a, not in group index image 52b. In this example, these are centerlines for groups 7, 15, 23, 31, and 39. Similarly, dotted lines extend outward from groups that have centerlines only in group index image 52b but not in group index image 52a. In this example, these are centerlines for groups 3, 11, 19, 27, and 35. Within each of the projected group index images 52a and 52b, these centerlines that are not shared are spaced apart from each other by a second distance D2 that is a second multiple of group size. As shown in FIG. 6, the second distance D2 is a distance that is 8 groups wide.

Spacing the centerlines apart in the arrangement shown in FIG. 6, with some centerlines shared and some not shared, has advantages that may not be readily apparent. The wider spacing of 8 groups is a second multiple of group size that is larger than the first multiple of group size that is used between common centerlines. This wider spacing between non-shared centerlines helps to reduce ambiguity in group identification. For example, with a certain p, when centerline image sequence size 1 is large enough, the distance of any adjacent 2 centerlines on any one centerline image (e.g., with p×l illumination pixels) will be large enough to unambiguously assign the detected centerline peaks in each recorded centerline image to the corresponding groups with the assumption that the surface depth is in a preset range with respect to a focal position. Thus, the centerline peaks of these non-shared lines can be checked for their presence in one of images 52a and 52b and absence in the other image.

According to the structured light system design and object tooth surface, each recorded centerline from group index images 52a and 52b is positioned between 2 neighbors. For example, the $m^{th}$ centerline is located to the left of the $(m-1)^{th}$ centerline and right of the $(m+1)^{th}$ centerline, for the example given wherein 1<m<40. Once the non-shared $3^{rd}$, $7^{th}$, $11^{th}$, $15^{th}$, $19^{th}$, $23^{rd}$, $27^{th}$, $31^{st}$, $35^{th}$, and $39^{th}$ centerlines have been successfully assigned, it is possible to assign centerline peaks of the shared $1^{st}$, $5^{th}$, $9^{th}$, $13^{th}$, $17^{th}$, $21^{st}$, $25^{th}$, $29^{th}$, $33^{rd}$, $37^{th}$ groups by dual neighbor referencing. For example, an unassigned centerline peak that is located between the $15^{th}$ and the $19^{th}$ assigned centerlines can be readily and unambiguously assigned to group 17.

The group mapping that is obtained from the first and second group index images forms a first set of mapped groups. For the example given in FIG. 6, the first set of mapped groups consists of all of the odd-numbered groups. After the odd-numbered groups have been mapped, the even numbered groups are then mapped using one of the multiline images, specifically, centered multiline image 76. As described previously, this is the one multiline image of the p multiline images that has the same centerline arrangement used for the group index images, e.g., with pixel p/2 illuminated in each group, as described previously with reference to FIG. 5. This image is one of the subset of p multiline images, described subsequently.

According to an alternate embodiment of the present disclosure, the group index images 52a and 52b are used to map the even-numbered groups as the first set of mapped groups, with corresponding spacing following the basic pattern described in FIG. 6. Then, a multiline image is used to map odd-numbered groups.

Multiline Images

As was noted with respect to the sequence shown in FIG. 3, a set of p multiline images is projected onto the surface, in addition to the group index images 52a and 52b. At least one of the multiline images is used for generating the group mapping and pixel level resolution; the other multiline images provide only pixel-level resolution for obtaining surface contour information. The single multiline image needed for group mapping can be a centered multiline image 76, as represented in the logic flow diagram of FIG. 3.

Figure 7A:
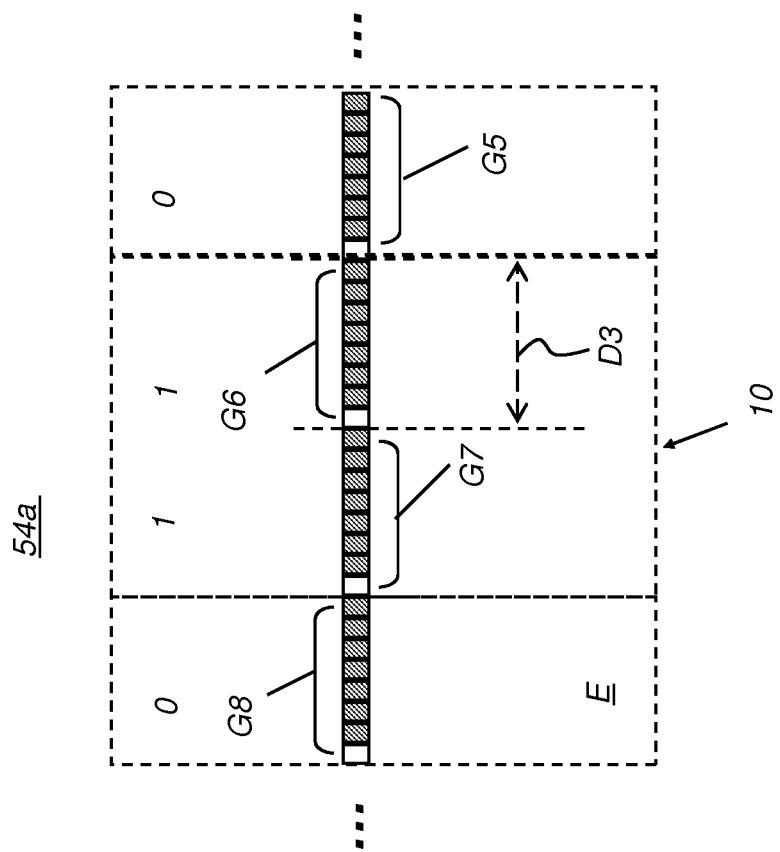
FIG. 7A shows a portion of the illumination array for forming a multiline image.
Figure 7B:
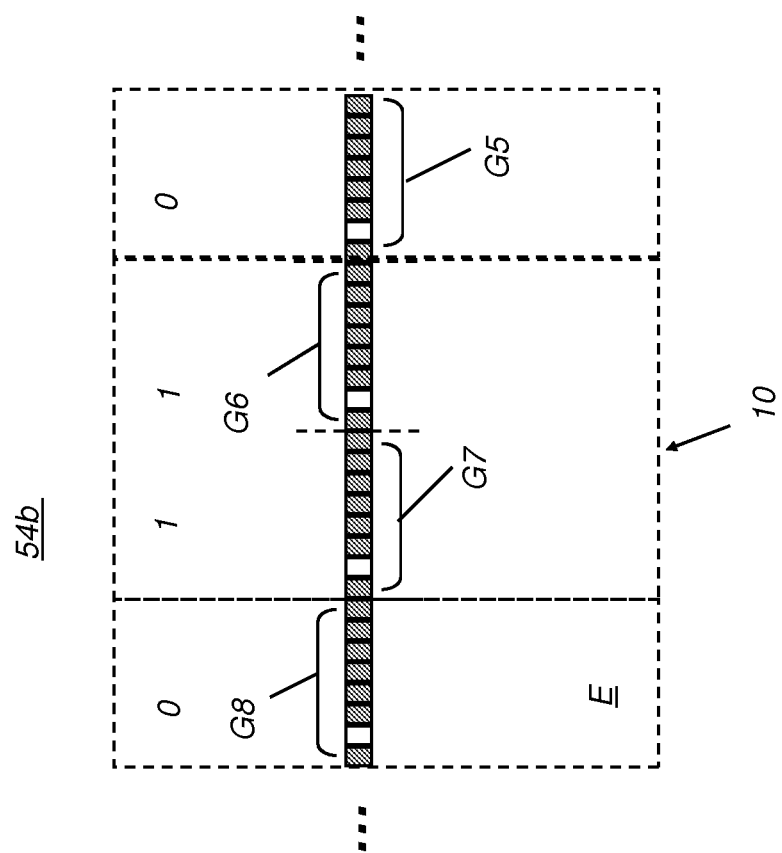
FIG. 7B shows another portion of the illumination array for forming a multiline image.

In the multiline images, one pixel for each group is illuminated at a time. The schematic diagram of FIG. 7A shows, for a single row of illumination array 10 shown in an enlarged portion E with groups G5, G6, G7, and G8, a portion of a first multiline image 54a in which the left-most pixel in each group is illuminated to form a line. FIG. 7B shows another multiline image 54b in which the next pixel in each group is illuminated. Where each group has 8 pixels, as in the examples shown herein, this sequence repeats so that there are at least 8 multiline images, one for each pixel in each group. Transitions from dark to light or from light to dark are only with respect to a single pixel width in a multiline image; each bright band of light that forms a line is a single pixel wide. Each multiline image projects a single line within each group. In general, where each group has a number p adjacent pixels, a subset of at least p/2 multiline images are projected onto the surface and recorded for surface contour imaging. In addition, more than 8 multiline images can be projected and recorded, in a cyclical or other sequencing arrangement. A group width distance D3 between illuminated pixels in each multiline image 54 extends over p pixels.

In an alternate embodiment, a subset of the set of p multiline images are projected for obtaining surface contour measurements to project a reduced number of lines within each group. Data interpolation can be applied to fill in the data for the individual lines in each group that were not projected. For example, in one embodiment, the group index images 52a and 52b and one of the multiline images is used for generating the group mapping; the remaining p−1 multiline images provide only pixel-level resolution for obtaining surface contour information.

Figure 8:
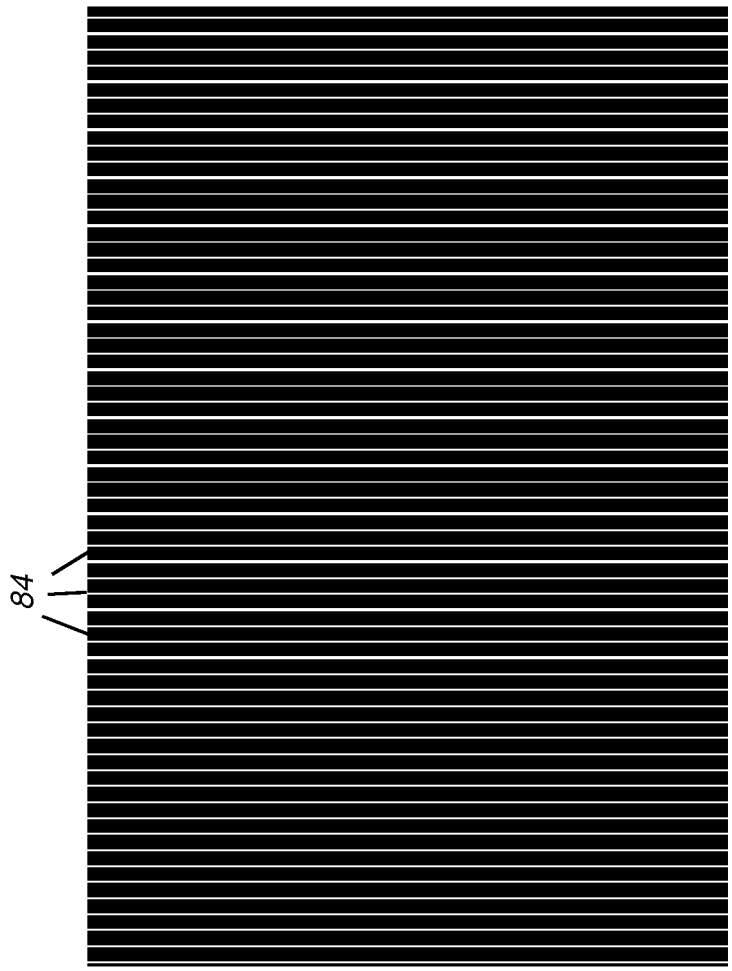
FIG. 8 is a plan view of an exemplary multiline image.
Figure 9:
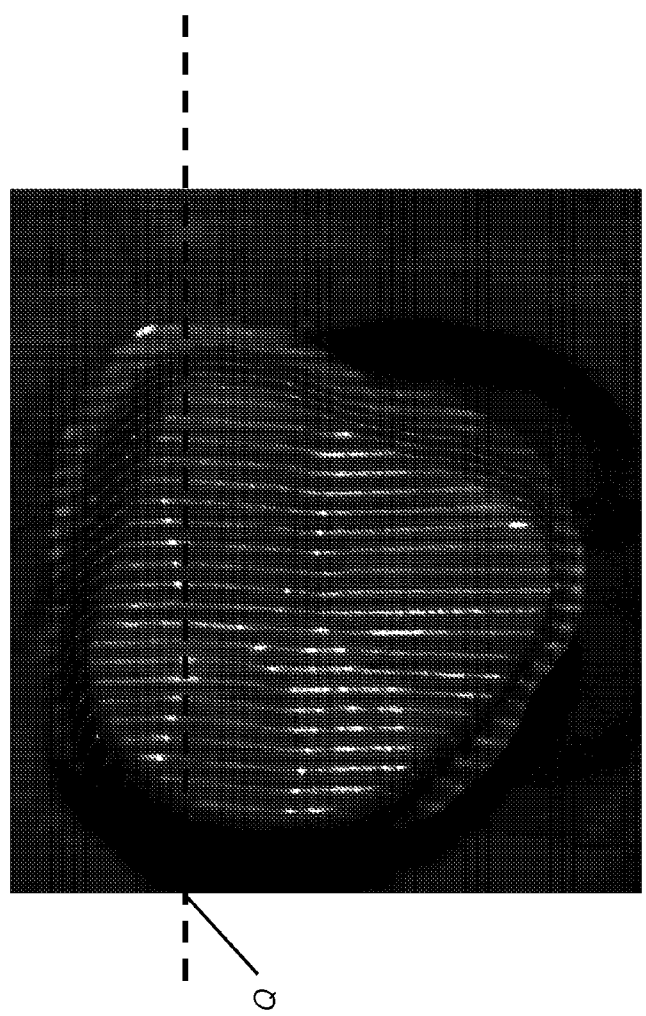
FIG. 9 is a plan view of a projected multiline image on a tooth.
Figure 10:
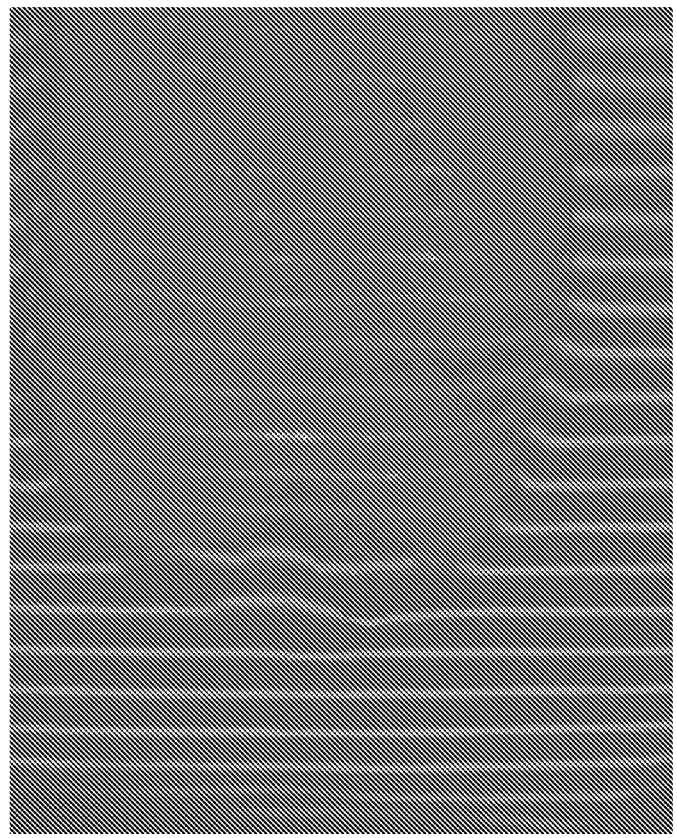
FIG. 10 is another plan view of a projected multiline image on a tooth.

FIG. 8 shows a multiline image 54 with a line 84 within each group as projected from illumination array 10. FIGS. 9 and 10 show exemplary multiline images 54 projected onto the surface 20 and recorded by imaging sensor array 30, respectively. The dashed line Q in FIG. 9 indicates one row of pixels on imaging sensor array 30.

Consistent with an embodiment of the present disclosure, each of the multiline images is analyzed as a set of independent rows, to locate each intensity peak in the row. This is done in two steps. Initially, a combination of smoothing filter and differentiating filter locates pixels where there is a peak signal. Then, a parabola is fit to the observed points around the identified pixel in order to locate the peak with sub-pixel accuracy. The background around the peak is also estimated to provide additional information on relative peak height. A candidate peak can be dropped from the list of peaks if it is too weak or too close to another peak. The result of the analysis is a long peak list (30,000 to 100,000 for a typical imaging sensor array) of precise locations where intensity peaks were observed.

For group mapping, the particular multiline image 54 that has the centerline of each group, with the p/2 pixel illuminated, forms the centered multiline image 76. Centered multiline image 76 provides the needed information to map the remaining group centerlines that were not obtained from group index images 52a and 52b. For the exemplary embodiment described previously, this means that the remaining even-numbered groups can be mapped using the multiline image 54 that has the centerline of each group, with the p/2 pixel illuminated. Using this technique, where group index images 52a and 52b identify each odd-numbered group, centered multiline image 76 identifies the interleaved even-numbered groups. In an alternate embodiment, using similar logic, where group index images 52a and 52b identify each even-numbered group, centered multiline image 76 identifies the remaining interleaved odd-numbered groups. To help resolve ambiguities, processing for group identification can use dual-neighbor referencing with finer resolution as group identification proceeds.

In an alternate embodiment, first group index images 52a and 52b can be used for a first set of groups (e.g., odd groups) and additional or second group index images can be used for a second set of groups (e.g., even groups) for generating the group mapping. Then, multiline images 54 can be used to provide pixel-level resolution for obtaining surface contour information.

There is some level of signal (a "cut-off point") in the flat image 38 (FIG. 3) that can be too low for accurate comparisons. This level can simply be set as a parameter for the processing software. It can also be calculated adaptively by finding all the peaks in the multiline image, as described subsequently, and noting the "flat" values at those peak positions. Pixels with levels below this cutoff point are simply declared to be indeterminate, having unknown states, and are not processed further.

Combining the Group Map and Peak List

In the absence of noise or errors, combination of group and peak data is driven by the list of peaks, which contains the peak location in x and y (e.g., pixel location along the row and the row number), the peak height, the peak width, and the image from which it came (multiline images 1 to p). For each peak, the group number from the nearest pixel in the group mapping is retrieved. The group number and image number are combined to calculate the line on the illuminator, 1 to 480 in a 480 line image. This gives three essential "pixel positions" for the peak: the x and y location on the imager and the x location on the illuminator, just as would be obtained from a single projected point.

An approximate position of the point on the tooth or other surface can then be calculated, using the three pixel positions and calibration parameters. These approximate positions are processed, using information known from calibration, to determine an accurate location (x, y, z) on the surface of the tooth or other object. All of these locations can be used to form the point cloud that is the final output of the combination algorithm.

Optional Dark and Flat Images

Dark and flat field images 36 and 38 are optionally obtained as described in the sequence of FIG. 3. These images can be averaged to provide a measure of intensity that is used as a threshold to differentiate bright from dark intensities to help improve the signal mapping in pixel assignment step 44 (FIG. 3).

It should be noted that the sequence of image projections and recording can be followed in any suitable order for the methods of the present invention. Moreover, multiline images and group index patterns can be interspersed, rather than obtained in any fixed order.

Forming a group mapping helps to resolve potential ambiguities in depth measurement. Embodiments of the present invention help to provide robust methods for group mapping without requiring projection, detection, and processing of an excessive number of binary images.

Figure 11B:
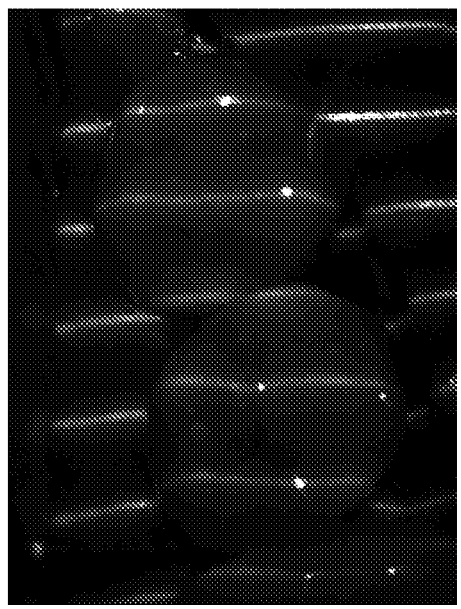
FIG. 11B shows a tooth image obtained using the illumination pattern of FIG. 11A.
Figure 11A:
FIG. 11A shows a portion of the illumination pattern that is projected in a group index image.

FIG. 11A shows the illumination pattern that is projected in one of the group index images 52. By way of example, FIG. 11B shows a portion of a corresponding tooth image 112 that is obtained from projection of group index image 102.

Figure 12B:
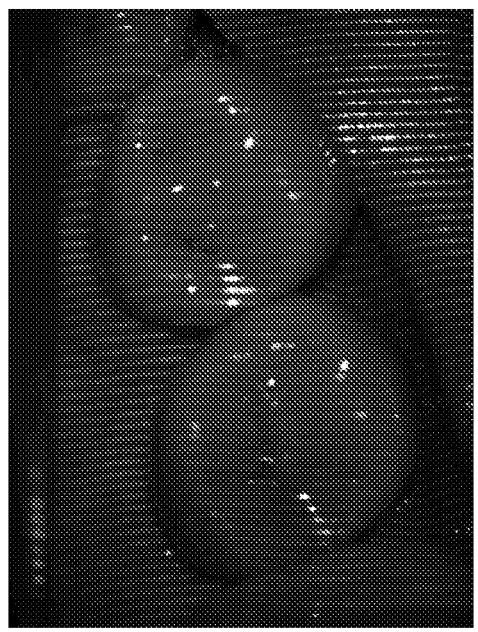
FIG. 12B shows a tooth image obtained using the illumination pattern of FIG. 12A.
Figure 12A:
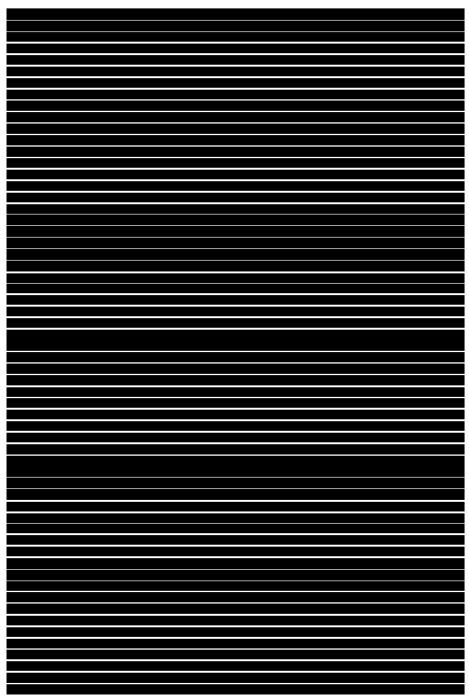
FIG. 12A shows the illumination pattern that is projected in a multiline image.

FIG. 12A shows the illumination pattern that is projected in one of the multiline images 54. By way of example, FIG. 12B shows a corresponding tooth image 116 that is obtained from projection of multiline image 54.

Embodiments of the present invention can employ different group sizes and arrangements, including specification of which sets of groups have pixels illuminated at any one time. For the sake of simplicity in the description of the image patterns that follow, an arbitrary group size of 8 pixels is used. The behavior of 128 pixels, in 16 groups with 8 pixels per group, is described. The 16 groups form an ordered set, in the terminology used herein. It can be appreciated that changes can be made in group size or in the number of groups that are members of an ordered set, within the scope of the present invention. The description that is given herein uses these exemplary values in differentiating group index images from multiline images.

Light intensity for each image can be the same; however, there can be advantages to changing intensity for different image types. Suitable adjustment of intensity can help to reduce the impact of scattered light, for example.

Consistent with an embodiment of the present invention, a computer executes a program with stored instructions that perform on image data accessed from an electronic memory. As can be appreciated by those skilled in the image processing arts, a computer program of an embodiment of the present invention can be utilized by a suitable, general-purpose computer system, such as a personal computer or workstation, as well as by a microprocessor or other dedicated processor or programmable logic device. However, many other types of computer systems can be used to execute the computer program of the present invention, including networked processors. The computer program for performing the method of the present invention may be stored in a computer readable storage medium. This medium may comprise, for example; magnetic storage media such as a magnetic disk (such as a hard drive) or magnetic tape or other portable type of magnetic disk; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

In the context of the present disclosure, the act of "recording" images means storing image data in some type of memory circuit in order to use this image data for subsequent processing. The recorded image data itself may be stored more permanently or discarded once it is no longer needed for further processing. An "ordered set" has its conventional meaning as used in set theory, relating to a set whose elements have a non-ambiguous ordering, such as the set of natural numbers that are ordered in an ascending sequence, for example.

It should be noted that the term "memory", equivalent to "computer-accessible memory" in the context of the present disclosure, can refer to any type of temporary or more enduring data storage workspace used for storing and operating upon image data and accessible to a computer system. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types. Computer-accessible memory of various types is provided on different components throughout the system for storing, processing, transferring, and displaying data, and for other functions.

In one embodiment, the apparatus 70 shown in FIG. 4, an intraoral camera or the like can implement, in hardware or control logic, the functionality and/or operations shown in or described with respect to FIG. 3. Although described herein as 1 pixel wide, the group index images 52a and 52b in certain exemplary embodiments can use two or more pixel wide lines.

In one embodiment there is provide a method and/or apparatus for mapping a sensor pixel array to an illumination pixel array according to a surface, executed at least in part on a computer and that can include forming a group mapping by assigning each pixel in a plurality of pixels on the sensor array to a corresponding group of an ordered set of groups on the illumination pixel array, wherein each group has a group width defined by a set of p adjacent pixels on the illumination pixel array and the ordered set has k groups by: projecting onto the surface and recording a first multiple group index image with a first pattern of lines and a second multiple group index image with a second pattern of lines, wherein lines that appear at identical positions in both the first pattern of lines and the second pattern of lines are evenly spaced from each other by a first distance that is a first multiple of group width p, wherein the first multiple is an integer greater than 1, and lines that appear only in either the first pattern of lines or the second pattern of lines are evenly spaced from each other by a second distance that is a second multiple of group size and that exceeds the first distance; projecting onto the surface and recording a third multiple group index image with a third pattern of lines and a fourth multiple group index image with a fourth pattern of lines, wherein lines that appear at identical positions in both the third pattern of lines and the fourth pattern of lines are evenly spaced from each other by a first distance, and lines that appear only in either the third pattern of lines or the fourth pattern of lines are evenly spaced from each other by a second distance that exceeds the third distance; and correlating lines in the first multiple group index image and the second multiple group index image to lines in the third multiple group index image and the fourth multiple group index image to generate the group mapping for all k groups and storing the correlation in a computer-accessible memory.

This application is related to commonly assigned U.S. Ser. No. 13/293,308, entitled 3-D INTRAORAL MEASUREMENTS USING OPTICAL MULTILINE METHOD to James Milch, incorporated herein by reference in its entirety.

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A method for mapping a sensor pixel array to an illumination pixel array according to a surface, the method executed at least in part on a computer and comprising:
   forming a group mapping by assigning each pixel in a plurality of pixels on the sensor array to a corresponding group of an ordered set of groups on the illumination pixel array, wherein each group has a group width defined by a set of p adjacent pixels on the illumination pixel array and the ordered set has k groups by:
   projecting onto the surface and recording a first multiple group index image with a first pattern of lines and a second multiple group index image with a second pattern of lines, wherein lines that appear at identical positions in both the first pattern of lines and the second pattern of lines are evenly spaced from each other by a first distance that is a first multiple of group width p, wherein the first multiple is an integer greater than 1, and lines that appear only in either the first pattern of lines or the second pattern of lines are evenly spaced from each other by a second distance that is a second multiple of group size and that exceeds the first distance;
   projecting onto the surface and recording a subset of a set of p multiline images, wherein each multiline image projects a line within each group and wherein the projected lines in each of the subset of p multiline images are evenly spaced apart by a group width of p pixels; and
   correlating lines in one of the recorded multiline images with lines from the first and second multiple group index images to generate the group mapping for all k groups and storing the correlation in a computer-accessible memory.

2. The method of claim 1 wherein correlating lines comprises:
   correlating lines in the first multiple group index image with lines in the second multiple group index image to generate a first set of mapped groups; and
   correlating lines of the first set of mapped groups with lines in at least one member of the subset of recorded multiline images.

3. The method of claim 2 further comprising checking for the presence of lines at predetermined positions in one or more of the recorded multiline images and the absence of lines at other positions in the first set of mapped groups.

4. The method of claim 1 further comprising displaying one or more of the first multiple group index image, the second multiple group index image or the recorded multiline images.

5. The method of claim 1 wherein the second distance is twice the first distance.

6. The method of claim 1 wherein the illumination pixel array is a liquid crystal device or a digital micromirror array device.

7. The method of claim 1 wherein forming the group map further comprises projecting and recording at least one dark field image and at least one flat field image.

8. The method of claim 1 further comprising computing and displaying surface contour data according to the recorded multiline images and the group mapping for all k groups.

9. The method of claim 1 wherein the subset of the set of p multiline images consists of a single multiline image.

10. A method for providing a surface contour image, the method executed at least in part by a computer and comprising:
    forming a group mapping by assigning each pixel in a plurality of pixels on the sensor array to a corresponding group of an ordered set of groups on the illumination pixel array, wherein each group has a group width defined by a set of p adjacent pixels on the illumination pixel array and the ordered set has k groups by:
    projecting and recording a first multiple group index image with a first pattern of lines and a second multiple group index image with a second pattern of lines, wherein there are lines that appear at identical positions in both the first and second pattern, and wherein lines that appear in both first and second patterns are evenly spaced from each other by a first distance that is a first multiple of group width p wherein the first multiple is an integer greater than 1, and lines that appear only in either the first or the second pattern are evenly spaced from each other by a second distance that is a second multiple of group size and that exceeds the first distance;
    projecting and recording a subset of a set of p multiline images, wherein each multiline image projects a line within each group and wherein the projected lines in each of the subset of p multiline images in the set are evenly spaced apart by a width of p pixels;
    correlating lines in one of the multiline images with lines from the first and second multiple group index images to generate the group mapping for all k groups and storing the correlation in a computer-accessible memory;
    detecting peak locations from the projected subset of p multiline images and forming the surface contour image according to the peak locations and group mapping; and
    displaying the surface contour image.

11. The method of claim 10 wherein correlating lines comprises
    correlating lines in the first multiple group index image with lines in the second multiple group index images to generate a first set of mapped groups; and
    correlating lines of the first set of mapped groups with lines in the one of the recorded multiline images.

12. The method of claim 10 further comprising checking for the presence of lines on the one of the recorded multiline images and the absence of lines in the first set of mapped groups.

13. The method of claim 10 wherein the illumination pixel array is a liquid crystal device or is a digital micromirror array device.

14. The method of claim 10 wherein forming the group map further comprises obtaining and recording at least one dark field image and at least one flat field image.

15. The method of claim 10 wherein the subset of the set of p multiline images consists of a single multiline image.

* * * * *